(12) United States Patent
Agrawal et al.

(10) Patent No.: US 10,960,501 B2
(45) Date of Patent: Mar. 30, 2021

(54) HEMOSTASIS VALVES AND METHODS FOR MAKING AND USING HEMOSTASIS VALVES

(71) Applicant: BOSTON SCIENTIFIC LIMITED, Hamilton (BM)

(72) Inventors: Sumit Agrawal, Haryana (IN); Mayank Bhatnagar, Delhi (IN); Alan James O'Flynn, County Tipperary (IE); Somashekar Reddy, Karnataka (IN); Henry J. Pepin, Loretto, MN (US); Peeyush Tomar, Uttar Pradesh (IN)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 162 days.

(21) Appl. No.: 15/903,747

(22) Filed: Feb. 23, 2018

(65) Prior Publication Data
US 2018/0256871 A1 Sep. 13, 2018

Related U.S. Application Data

(60) Provisional application No. 62/470,659, filed on Mar. 13, 2017.

(51) Int. Cl.
*B23P 15/00* (2006.01)
*A61M 39/06* (2006.01)

(52) U.S. Cl.
CPC ............ *B23P 15/001* (2013.01); *A61M 39/06* (2013.01); *A61M 39/0693* (2013.01);
(Continued)

(58) Field of Classification Search
CPC .. B23P 15/001; A61M 39/0693; A61M 39/06; A61M 2039/0633; A61M 2039/1044
See application file for complete search history.

(56) References Cited

U.S. PATENT DOCUMENTS

| 2,023,267 A | 12/1935 | De Saint Rapt et al. |
| 2,833,568 A | 5/1958 | Corsette |

(Continued)

FOREIGN PATENT DOCUMENTS

| DE | 29701600 U1 | 7/1997 |
| EP | 0567142 A2 | 10/1993 |

(Continued)

OTHER PUBLICATIONS

PCT Search Report and Written Opinion for PCT/US2009/039396 dated Apr. 3, 2009.

(Continued)

*Primary Examiner* — Christopher J Besler
(74) *Attorney, Agent, or Firm* — Seager, Tufte & Wickhem LLP.

(57) ABSTRACT

Hemostasis valves and methods for making and using hemostasis valves are disclosed. An example method for assembling a hemostasis valve may include positioning a plunger along a threaded proximal end region of a main body. The threaded proximal end region may include one or more threads and an axial slot extending through the one or more threads. The method may also include advancing the plunger along the threaded proximal end region to a position where a proximal end of the plunger is disposed distally of at least a portion of the one or more threads and disposing a nut adjacent to the threaded proximal end region. The method may also include aligning an alignment tab of the nut with the axial slot, engaging the nut with the one or more threads while the alignment tab is aligned with the axial slot, and rotating the nut 45-270°.

11 Claims, 13 Drawing Sheets

(52) U.S. Cl.
CPC . *A61M 2039/062* (2013.01); *A61M 2039/064* (2013.01); *A61M 2039/0633* (2013.01); *A61M 2039/0686* (2013.01)

(56) References Cited

U.S. PATENT DOCUMENTS

| | | | |
|---|---|---|---|
| 3,095,175 A | 6/1963 | Taisho |
| 3,180,334 A | 4/1965 | Glenn |
| 3,685,786 A | 8/1972 | Woodson |
| 4,000,739 A | 1/1977 | Stevens |
| 4,177,814 A | 12/1979 | Knepshield et al. |
| 4,240,411 A | 12/1980 | Hosono |
| 4,424,833 A | 1/1984 | Spector et al. |
| 4,430,081 A | 2/1984 | Timmermans |
| 4,436,519 A | 3/1984 | O'Neill |
| 4,610,655 A | 9/1986 | Mueller |
| 4,612,010 A | 9/1986 | Hamacher et al. |
| 4,615,531 A | 10/1986 | Green |
| 4,626,245 A | 12/1986 | Weinstein |
| 4,629,450 A | 12/1986 | Suzuki et al. |
| 4,655,752 A | 4/1987 | Honkanen et al. |
| 4,673,393 A | 6/1987 | Suzuki et al. |
| 4,705,511 A | 11/1987 | Kocak |
| 4,723,550 A | 2/1988 | Bales et al. |
| 4,726,374 A | 2/1988 | Bales et al. |
| 4,798,594 A | 1/1989 | Hillstead |
| 4,857,062 A | 8/1989 | Russell |
| 4,875,062 A | 10/1989 | Rakov |
| 4,895,346 A | 1/1990 | Steigerwald |
| 4,895,565 A | 1/1990 | Hillstead |
| 4,909,798 A | 3/1990 | Fleischhaker et al. |
| 4,917,668 A | 4/1990 | Haindl |
| 4,925,450 A | 5/1990 | Imonti et al. |
| 4,932,114 A | 6/1990 | Morse et al. |
| 4,932,633 A | 6/1990 | Johnson et al. |
| 4,960,412 A | 10/1990 | Fink |
| 4,978,341 A | 12/1990 | Niederhauser |
| 5,000,745 A | 3/1991 | Guest et al. |
| 5,009,391 A | 4/1991 | Steigerwald |
| 5,030,206 A | 7/1991 | Lander |
| 5,041,095 A | 8/1991 | Littrell |
| 5,049,071 A | 9/1991 | Davis et al. |
| 5,059,186 A | 10/1991 | Yamamoto et al. |
| 5,060,987 A | 10/1991 | Miller |
| 5,078,433 A | 1/1992 | Morse et al. |
| 5,078,688 A | 1/1992 | Lobodzinksi et al. |
| 5,098,393 A | 3/1992 | Amplatz et al. |
| 5,106,054 A | 4/1992 | Mollenauer et al. |
| 5,114,408 A | 5/1992 | Fleischhaker et al. |
| 5,125,903 A | 6/1992 | McLaughlin et al. |
| 5,135,492 A | 8/1992 | Melker et al. |
| 5,149,327 A | 9/1992 | Oshiyama |
| 5,154,701 A | 10/1992 | Cheer et al. |
| 5,158,553 A | 10/1992 | Berry et al. |
| 5,161,773 A | 11/1992 | Tower |
| 5,167,636 A | 12/1992 | Clement |
| 5,167,637 A | 12/1992 | Okada et al. |
| 5,176,652 A | 1/1993 | Littrell |
| 5,195,980 A | 3/1993 | Catlin |
| 5,197,463 A | 3/1993 | Jeshuran |
| 5,203,774 A | 4/1993 | Gilson et al. |
| 5,205,831 A | 4/1993 | Ryan et al. |
| 5,207,656 A | 5/1993 | Kranys |
| 5,224,929 A | 7/1993 | Remiszewski |
| 5,241,990 A | 9/1993 | Cook |
| 5,269,764 A | 12/1993 | Vetter et al. |
| 5,269,771 A | 12/1993 | Thomas et al. |
| 5,273,546 A | 12/1993 | Mclaughlin et al. |
| 5,282,790 A | 2/1994 | Clement |
| 5,299,843 A | 4/1994 | Weigl et al. |
| 5,324,271 A | 6/1994 | Abiuso et al. |
| 5,338,313 A | 8/1994 | Mollenauer et al. |
| 5,350,205 A | 9/1994 | Aldridge et al. |
| 5,350,364 A | 9/1994 | Stephens et al. |
| 5,352,215 A | 10/1994 | Thome et al. |
| 5,356,394 A | 10/1994 | Farley et al. |
| 5,364,371 A | 11/1994 | Kamen |
| 5,376,077 A | 12/1994 | Gomringer |
| 5,382,230 A | 1/1995 | Bonn |
| 5,383,860 A | 1/1995 | Lau |
| 5,389,090 A | 2/1995 | Fischell et al. |
| 5,395,349 A | 3/1995 | Quiachon et al. |
| 5,460,615 A | 10/1995 | Storz |
| 5,514,109 A | 5/1996 | Mollenauer et al. |
| 5,520,655 A | 5/1996 | Davila et al. |
| 5,542,933 A | 8/1996 | Marks |
| 5,562,611 A | 10/1996 | Transue |
| 5,569,208 A | 10/1996 | Woelpper et al. |
| 5,575,767 A | 11/1996 | Stevens |
| 5,584,314 A | 12/1996 | Bron |
| 5,591,137 A | 1/1997 | Stevens |
| 5,599,327 A | 2/1997 | Sugahara et al. |
| 5,643,227 A | 7/1997 | Stevens |
| 5,651,170 A | 7/1997 | Stevens |
| 5,693,025 A | 12/1997 | Stevens |
| 5,779,697 A | 7/1998 | Glowa et al. |
| 5,858,007 A | 1/1999 | Fagan et al. |
| 5,911,710 A | 6/1999 | Barry et al. |
| 5,921,968 A | 7/1999 | Lampropoulos et al. |
| 5,935,112 A | 8/1999 | Stevens et al. |
| 5,935,122 A | 8/1999 | Fourkas et al. |
| 5,992,899 A | 11/1999 | Strowe |
| 6,024,729 A | 2/2000 | Dehdashtian et al. |
| 6,149,632 A | 11/2000 | Landuyt |
| 6,277,100 B1 | 8/2001 | Raulerson et al. |
| 6,287,280 B1 | 9/2001 | Lampropoulos et al. |
| 6,331,176 B1 | 12/2001 | Becker et al. |
| 6,402,723 B1 | 6/2002 | Lampropoulos et al. |
| 6,458,103 B1 | 10/2002 | Albert et al. |
| 6,551,283 B1 | 4/2003 | Guo et al. |
| 6,572,590 B1 | 6/2003 | Stevens et al. |
| 6,632,200 B2 | 10/2003 | Guo et al. |
| 6,695,818 B2 | 2/2004 | Wollschlger |
| 6,986,749 B2 | 1/2006 | Wollschlger |
| 7,081,106 B1 | 7/2006 | Guo et al. |
| 7,172,580 B2 | 2/2007 | Hruska et al. |
| 7,938,809 B2 | 5/2011 | Lampropoulos et al. |
| 8,777,893 B2 | 7/2014 | Malewicz |
| 9,114,242 B2 * | 8/2015 | Fangrow ............ A61M 39/1011 |
| 9,592,372 B2 | 3/2017 | Myers |
| 2001/0021825 A1 | 9/2001 | Becker et al. |
| 2002/0010425 A1 | 1/2002 | Guo et al. |
| 2004/0172008 A1 | 9/2004 | Layer |
| 2004/0210194 A1 | 10/2004 | Bonnette et al. |
| 2005/0033239 A1 | 2/2005 | Argentine |
| 2005/0171479 A1 | 8/2005 | Hruska et al. |
| 2007/0106262 A1 | 5/2007 | Becker et al. |
| 2008/0157017 A1 | 7/2008 | Macatangay et al. |
| 2008/0208175 A1 | 8/2008 | Beckman et al. |
| 2009/0259200 A1 | 10/2009 | Lampropoulos et al. |
| 2012/0123392 A1 * | 5/2012 | McKinnon ............ A61M 39/10 604/533 |
| 2013/0006176 A1 | 1/2013 | Miller |
| 2013/0304026 A1 * | 11/2013 | Luther ................. A61M 39/06 604/506 |
| 2014/0207083 A1 | 7/2014 | Pessin |
| 2018/0126143 A1 | 5/2018 | Agrawal et al. |

FOREIGN PATENT DOCUMENTS

| | | | |
|---|---|---|---|
| WO | 9813083 A1 | 4/1998 |
| WO | 9945983 A1 | 9/1999 |
| WO | 0062844 A1 | 10/2000 |
| WO | 0117587 A1 | 3/2001 |
| WO | 2005018732 A1 | 3/2005 |
| WO | 2009139981 A2 | 11/2009 |

OTHER PUBLICATIONS

International Search Report and Written Opinion dated Jun. 20, 2018 for International Application No. PCT/US2018/019712.
International Search Report and Written Opinion for Application No. PCT/US2018/020202, 14 pages, dated May 25, 2018.

(56) References Cited

OTHER PUBLICATIONS

International Search Report and Written Opinion for Application No. PCT/US2018/020214, 17 pages, dated May 15, 2018.
International Search Report and Written Opinion for Application No. PCT/US2018/019674, 13 pages, dated Jun. 13, 2018.
International Search Report and Written Opinion for Application No. PCT/US2018/019479, 13 pages, dated May 22, 2018.

* cited by examiner

HEMOSTASIS VALVES AND METHODS FOR MAKING AND USING HEMOSTASIS VALVES

CROSS REFERENCE TO RELATED APPLICATIONS

This application claims the benefit of U.S. Provisional Patent Application Ser. No. 62/470,659 filed on Mar. 13, 2017, the disclosure of which is incorporated herein by reference.

TECHNICAL FIELD

The present disclosure pertains to medical devices, and methods for manufacturing medical devices. More particularly, the present disclosure pertains to hemostasis valves and methods for making and using hemostasis valves.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A method for assembling a hemostasis valve is disclosed. The method comprises: positioning a plunger along a threaded proximal end region of a main body; wherein threaded proximal end region of the main body includes one or more threads and an axial slot extending through the one or more threads; advancing the plunger along the threaded proximal end region of the main body to a position where a proximal end of the plunger is disposed distally of at least a portion of the one or more threads; disposing a nut adjacent to the threaded proximal end region of the main body, the nut having an alignment tab formed thereon; aligning the alignment tab with the axial slot; engaging the nut with the one or more threads while the alignment tab is aligned with the axial slot; and rotating the nut 45-270° relative to the threaded proximal end region of the main body.

Alternatively or additionally to any of the embodiments above, further comprising disposing a first seal member within the threaded proximal end region of the main body.

Alternatively or additionally to any of the embodiments above, further comprising disposing a cartridge at least partially within the threaded proximal end region of the main body, the cartridge including a second seal member.

Alternatively or additionally to any of the embodiments above, rotating the nut 45-270° relative to the threaded proximal end region of the main body engages the nut with the cartridge.

Alternatively or additionally to any of the embodiments above, further comprising moving the plunger proximally relative to the threaded proximal end region of the main body.

Alternatively or additionally to any of the embodiments above, further comprising disposing a spring within the plunger.

Alternatively or additionally to any of the embodiments above, further comprising securing a plunger cap to the plunger.

Alternatively or additionally to any of the embodiments above, the threaded proximal end region of the main body has a first locking indicator.

Alternatively or additionally to any of the embodiments above, the plunger includes a second locking indicator and wherein positioning a plunger along a threaded proximal end region of a main body includes aligning the first locking indicator with the second locking indicator.

Alternatively or additionally to any of the embodiments above, rotating the nut 45-270° relative to the threaded proximal end region of the main body includes rotating the nut 90-180° relative to the threaded proximal end region of the main body.

Alternatively or additionally to any of the embodiments above, rotating the nut 45-270° relative to the threaded proximal end region of the main body includes rotating the nut 180° relative to the threaded proximal end region of the main body.

A method for assembling a hemostasis valve is disclosed. The method comprises: advancing a plunger along a threaded proximal end region of a main body; wherein the threaded proximal end region has one or more threads and an axial slot; wherein advancing the plunger along a threaded proximal end region of a main body includes advancing the plunger to a position where a proximal end of the plunger is disposed distally of at least a portion of the one or more threads; engaging a nut with the threaded proximal end region of the main body, the nut having an alignment tab formed thereon; aligning the alignment tab with the axial slot; and rotating the nut 90-180° relative to the threaded proximal end region of the main body.

Alternatively or additionally to any of the embodiments above, further comprising disposing a first seal member within the threaded proximal end region of the main body and further comprising disposing a cartridge at least partially within the threaded proximal end region of the main body, the cartridge including a second seal member.

Alternatively or additionally to any of the embodiments above, rotating the nut 45-270° relative to the threaded proximal end region of the main body engages the nut with the cartridge.

Alternatively or additionally to any of the embodiments above, further comprising moving the plunger proximally relative to the threaded proximal end region of the main body.

Alternatively or additionally to any of the embodiments above, further comprising disposing a spring within the plunger and securing a plunger cap to the plunger.

Alternatively or additionally to any of the embodiments above, the threaded proximal end region of the main body has a first locking indicator, wherein the plunger includes a second locking indicator, and wherein positioning a plunger along a threaded proximal end region of a main body includes aligning the first locking indicator with the second locking indicator.

Alternatively or additionally to any of the embodiments above, rotating the nut 90-180° relative to the threaded proximal end region of the main body includes rotating the nut 180° relative to the threaded proximal end region of the main body.

A method for assembling a hemostasis valve is disclosed. The method comprises: disposing a cartridge at least partially within a threaded proximal end region of a main body; wherein the proximal end region of the main body has an axial slot formed therein; engaging a nut with the threaded proximal end region of the main body, the nut having an alignment slot formed therein; aligning the alignment slot with the axial slot; rotating the nut 90-180° relative to the threaded proximal end region of the main body; and coupling a plunger to the main body.

Alternatively or additionally to any of the embodiments above, rotating the nut 90-180° relative to the threaded proximal end region of the main body includes rotating the nut 180° relative to the threaded proximal end region of the main body.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
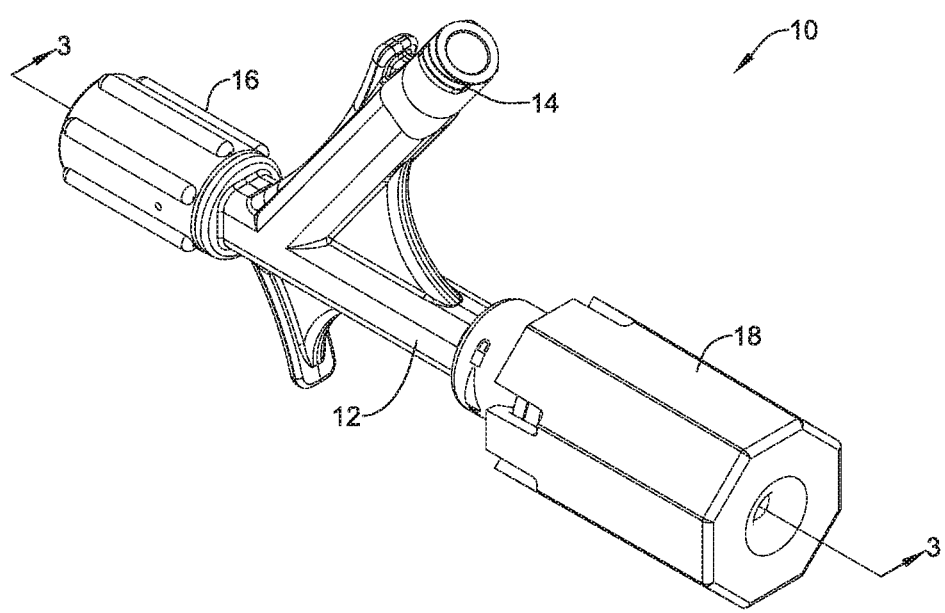
FIG. 1 is a perspective view of an example hemostasis valve.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, for example intravascular procedures, utilize medical devices within body lumens. For example, some intravascular procedures include the placement of a guidewire, guide catheter, interventional device, or the like in a blood vessel. Because fluid under pressure (e.g., blood) is present within the blood vessel, fluid could travel along or through the medical device and escape or leak from the patient. In some instances, it may be desirable to dispose a hemostasis valve or hemostasis valve assembly at the proximal end of a medical device to reduce or otherwise limit the leaking of fluids/blood from the proximal end of the device.

An example hemostasis valve 10 is shown in FIG. 1. The hemostasis valve 10 may include a main body 12. The main body 12 may include a side port 14. The side port 14 may be connected to another device such as an infusion device, an inflation device, or the like. An adapter 16 may be coupled to the distal end of the main body 12. The adapter 16 may be used to couple the hemostasis valve 10 to a device such as a catheter. A plunger 18 may be coupled to the proximal end of the main body 12. The plunger 18 may be used to activate or otherwise close a seal (e.g., as discussed herein) within the hemostasis valve 10. These and other features of the hemostasis valve 10 are discussed herein.

Figure 2:
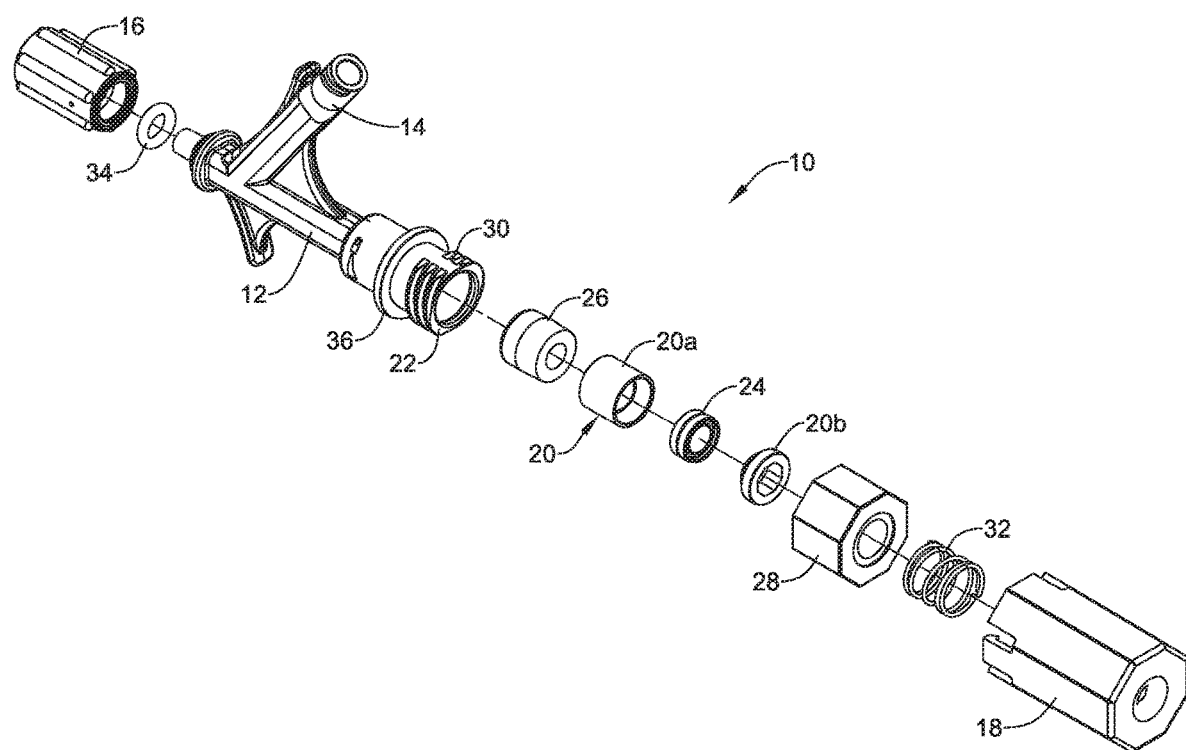
FIG. 2 is an exploded view of an example hemostasis valve.

FIG. 2 is an exploded view of the hemostasis valve 10. Here, the various components of the hemostasis valve 10 can be seen. For example, the hemostasis valve 10 may include a cartridge 20. The cartridge 20, which may include two pieces 20a, 20b that are coupled to one another (e.g., press fit, thermally bonded, adhesively bonded, etc.), may be arranged so that at least a portion thereof can be disposed within a proximal end region 22 of the main body 12. A first seal member 24 may be disposed within the cartridge 20. A second seal member 26 may be disposed within the proximal end region 22 of the main body 12. In at least some instances, the second seal member 26 may be disposed distally of the cartridge 20. The second seal member 26 may include a textured distal surface, grooves or wells formed therein, or the like. In addition or in the alternative, the second seal member 26 may include a proximal region with a reduced diameter. A nut 28 may be coupled to the proximal end region 22 of the main body 12, for example at one or more threads 30 formed along the proximal end region 22.

Other features of the hemostasis valve 10 that can be seen in FIG. 2 include a spring member 32 and an O-ring 34. The spring member 32 may be coupled to the plunger 18. In at least some instances, the spring member 32 may be designed to exert a proximally directed force on the plunger 18. The O-ring 34 may be positioned adjacent to the adapter 16. In addition, a ring member or "snap ring" 36 may be disposed along the proximal end region 22 of the main body 12.

Figure 3:
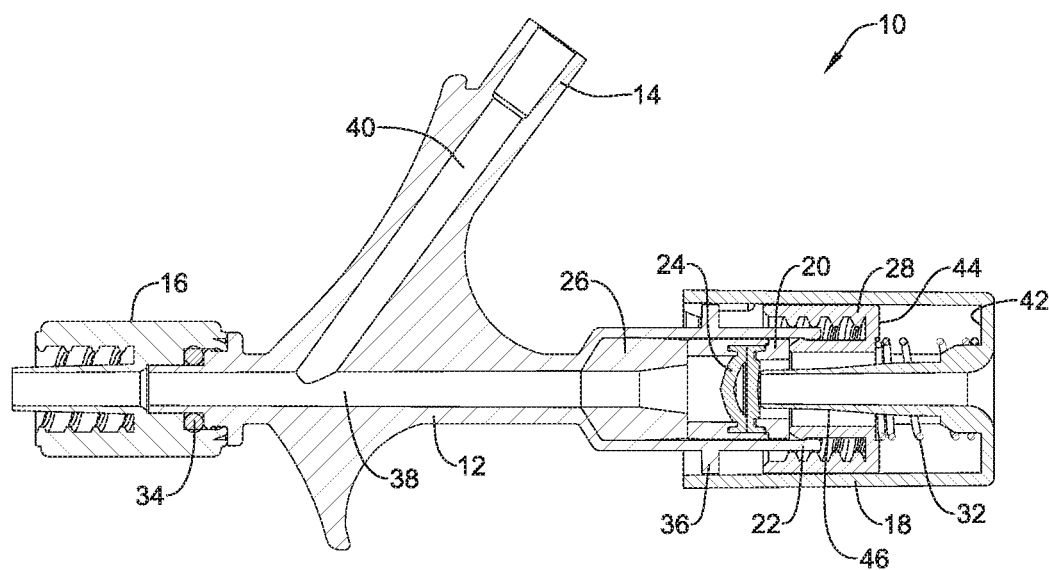
FIG. 3 is a cross-sectional view taken through line 3-3 in FIG. 1.

FIG. 3 is a cross-sectional view the hemostasis valve 10. Here some of the structural features of the hemostasis valve 10 can be seen. For example, the hemostasis valve 10 may include a central lumen 38. In general, the central lumen 38 is designed to be placed into fluid communication with one or more lumens of a device coupled to the adapter 16. A second or infusion lumen 40 may be defined adjacent to the side port 14. The second lumen 40 may be in fluid communication with the central lumen 38.

As indicated above, the hemostasis valve 10 is designed so that it may be coupled to another device. For example, the adapter 16, which may take the form of a Tuohy-Borst or other type of connector, may be engaged with the proximal end of the other device. When connected (and with the plunger 18 in the configuration shown in FIG. 3), the second seal member 26 may be in an open state or configuration. Conversely, the first seal member 24 may be in a closed or sealed configuration when the hemostasis valve 10 is connected to the other device (and with the plunger 18 in the configuration shown in FIG. 3).

Collectively, when the hemostasis valve 10 is connected to another device and in the configuration shown in FIG. 3, the hemostasis valve 10 is able to substantially hold a fluid-tight seal that substantially prevents the backflow and/or leakage of body fluids (e.g., blood). At some point during a medical intervention, it may be desirable to infuse additional fluids such as contrast media through the hemostasis valve 10. This may include attaching an infusion device to the side port 14. Because the first seal member 24 may be designed to substantially prevent the backflow and/or leakage of relatively-low pressure fluids, if the infusion device infuses fluids at a relatively high pressure, it is possible that the infusion fluid may be able to flow through the first seal member 24.

Figure 4:
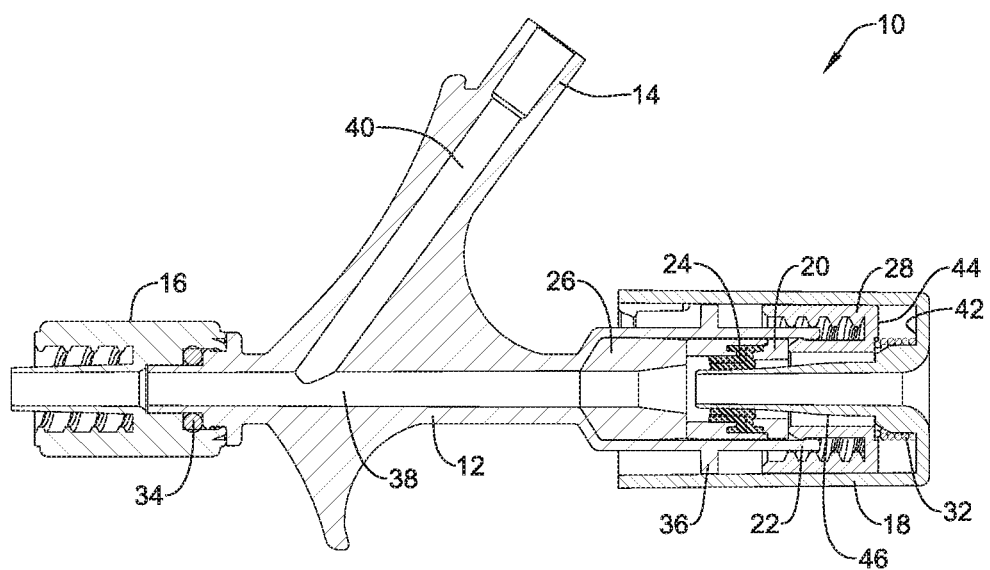
FIG. 4 is a cross-sectional view of an example hemostasis valve.
Figure 5A:
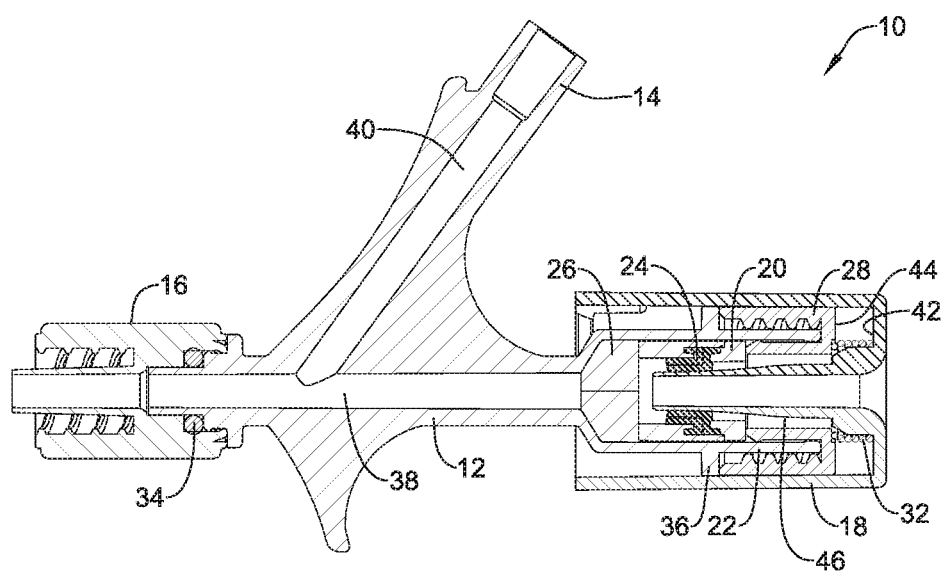
FIGS. 5A-5B is a cross-sectional view of an example hemostasis valve.
Figure 5B:
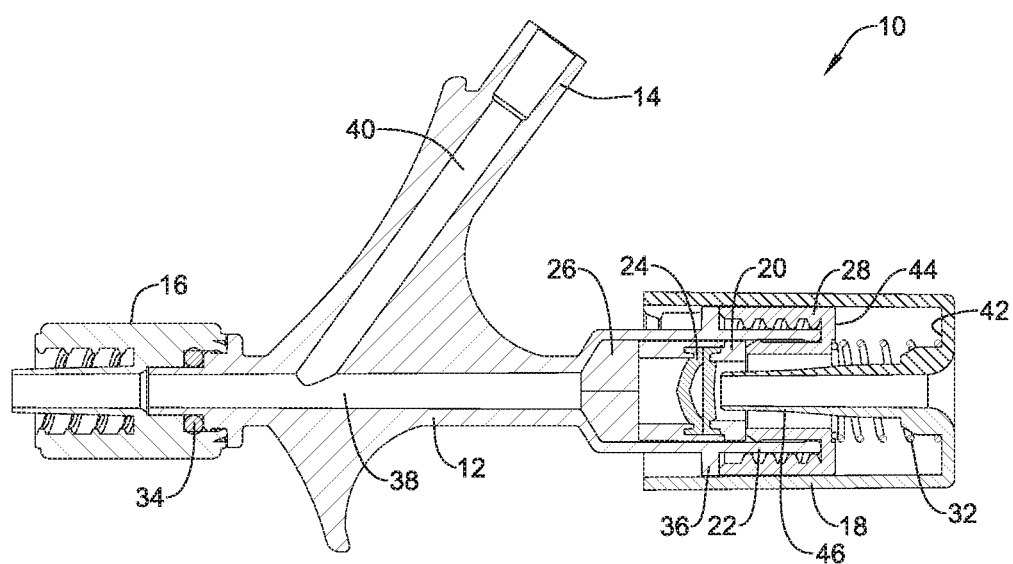
Figure 6:
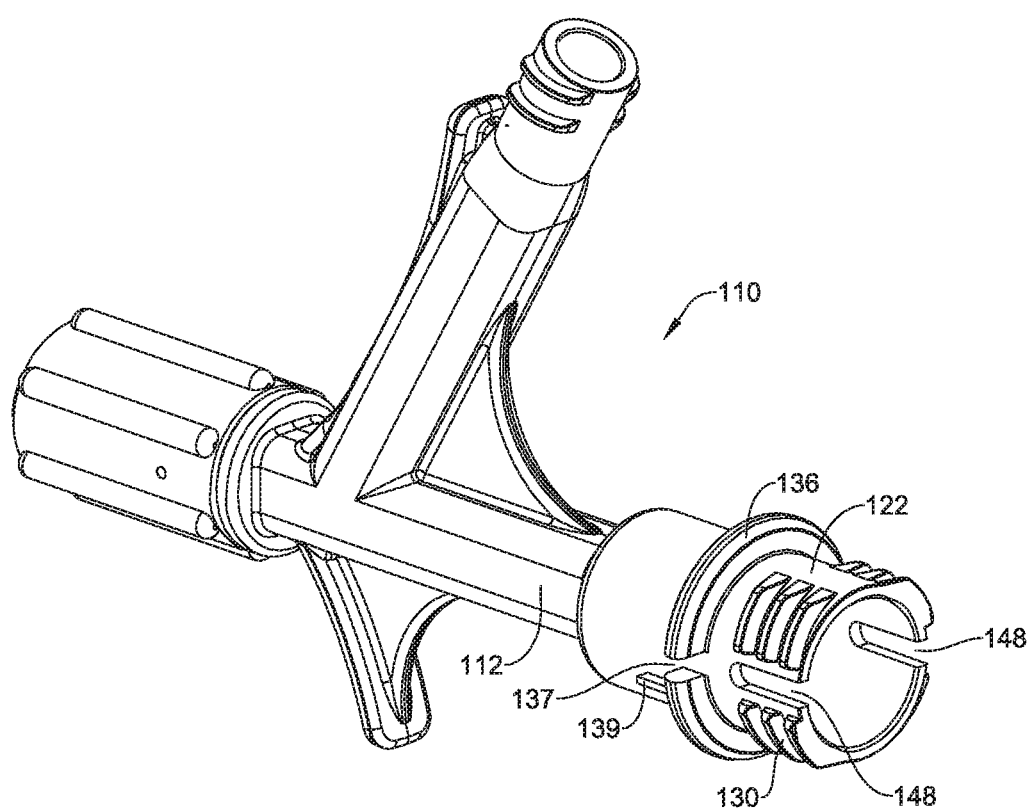
FIG. 6-10 illustrate an example hemostasis valve and an example method for assembling the hemostasis valve.

In order to prevent backflow of relatively high pressure fluids, the hemostasis valve 10 can be actuated to close or "seal" the second seal member 26. To do so, the plunger 18 may initially be urged distally until a distally-facing, proximal end surface or cap 42 of the plunger 18 is disposed adjacent to a proximal end region 44 of the nut 28 as shown in FIG. 4. When doing so, a tubular region 46 of the plunger 18 may extend through (and open) the first seal member 24. In addition, a portion of the plunger 18 may move distally beyond the ring member 36. With the cap 42 of the plunger 18 disposed adjacent to the nut 28, the plunger 18 can be rotated (e.g., in a clockwise direction) to close the second seal member 26 as shown in FIG. 5A. This rotation may cause the nut 28 to rotate and move distally. Because the distal end region of the nut 28 may be engaged with the cartridge 20, distal movement of the nut 28 urges the cartridge 20 distally within the proximal end region 22 of the main body 12 such that the cartridge 20 engages and deforms the second seal member 26, thereby shifting the second seal member 26 to the closed or sealed configuration. The plunger 18 may be released or otherwise allowed to move proximally, as shown in FIG. 5B, which may reclose the first seal member 24 (while the second seal member 26 remains closed).

For the purposes of this disclosure, "clockwise" rotation of the plunger 18 and/or nut 28 may be understood as rotation of the plunger 18 in a clockwise direction relative to the main body 12 when looking at the plunger 18 from its proximal end. Similarly, "counter-clockwise" rotation of the plunger 18 and/or nut 28 may be understood as rotation of the plunger 18 in a counter-clockwise direction relative to the main body 12 when looking at the plunger 18 from its proximal end. This convention for clockwise/counter-clockwise is used throughout this disclosure.

The process for assembling the hemostasis valve 10 (and/or other hemostasis valves disclosed herein) is generally designed so that assembly can occur using mechanical fittings (e.g., using only mechanical fitting such that no gluing may be necessary). In addition, the process is designed so that the nut 28 can apply a suitable amount of force onto the cartridge 20 so that the cartridge 20 is seated in the desired manner within the proximal end region 22 of the main body 12 and so that the second seal member 26 remains open. Some additional details of the assembly process are described herein.

FIGS. 6-10 illustrate a portion of an example hemostasis valve 110 that may be similar to other hemostasis valves disclosed herein and illustrate the process for assembling the hemostasis valve 110. In at least some instances, the proximal end region 122 of the main body 112 may include threads 130 and one or more axial slots 148. In this example, the proximal end region 122 includes a pair of opposing axial slots 148. However, differing numbers and/or arrangements of axial slots 148 are contemplated. The axial slots 148 may be designed to engage projections 150, as discussed herein, on the cartridge 120 so that rotation of the cartridge 120 during actuation of a plunger 118 and/or a nut 128 can be reduced or eliminated. A ring member 136 may also be disposed adjacent to the proximal end region 122. The ring member 136 may have an opening 137 formed therein. A locking rib 139 may be disposed adjacent to the ring member 136. The locking rib 139 may be designed to prevent counter-clockwise rotation of the plunger 118 and/or the nut 128 in a manner that could cause the nut 128 to become unthreaded from the proximal end region 122.

Figure 7:
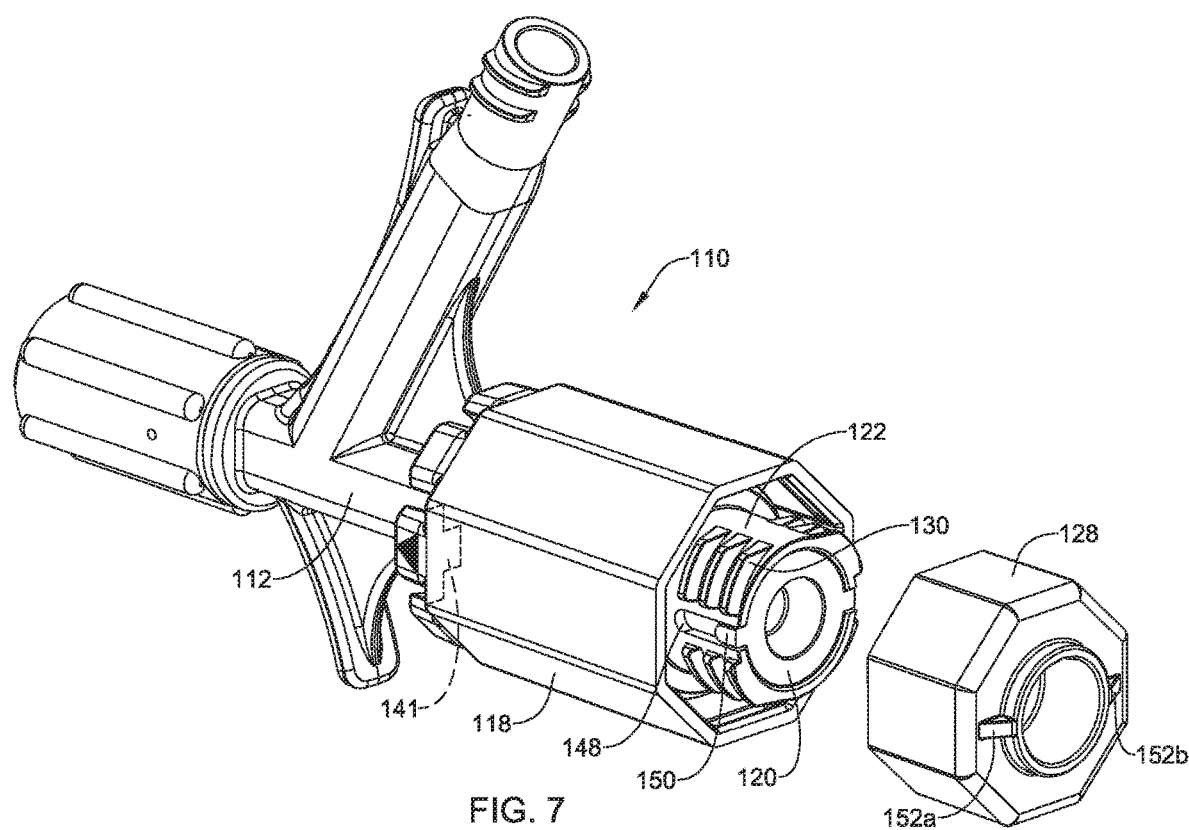
Figure 8:
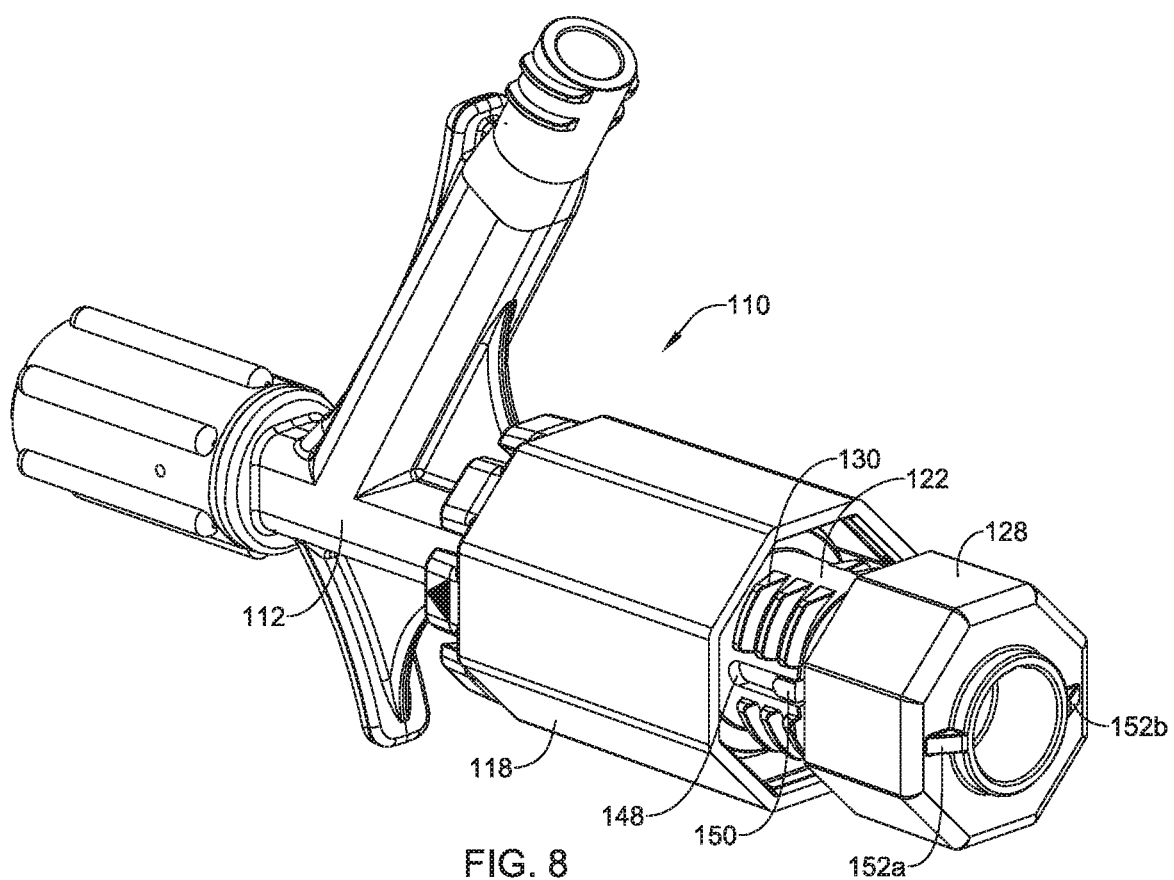

The process for assembling the hemostasis valve 110 may include disposing a second seal member (not shown, but may be similar to the second seal member 26 disclosed herein) and a cartridge 120 within the proximal end region 122 of the main body 112. The cartridge 120 may be similar in form to other cartridges disclosed herein and may include a first seal member (e.g., similar to the first seal member 24). In addition, the plunger 118 may be advanced along the proximal end region 122 of the main body 112 as shown in FIG. 7. When doing so, the plunger 118 may be advanced distally beyond at least a portion of the threads 130 so that the threads 130 are exposed proximally of the plunger 118 (e.g., which may include advancing a locking tab 141 formed along the plunger 118 through the opening 137 of the ring member 136). This allows the nut 128 to be placed into contact with or otherwise engaged with the proximal end region 122 of the main body 112 and/or the threads 130 as shown in FIG. 8. It may be desirable for the nut 128 to be secured to the proximal end region 122 of the main body 112 by, for example, threadably engaging the nut 128 with the threads 130 along the proximal end region 122. In addition, it may also be desirable for the nut 128 to be threaded onto the threads 130 in such a manner that the nut 128 engages and applies a suitable amount of force onto the cartridge 120 so that the cartridge 120 is held in place within the proximal end region 122. In addition, the force applied to the cartridge 120 may also apply a suitable amount of force onto the second seal member (not shown) such that the second seal member is also suitably held in place.

Figure 9:
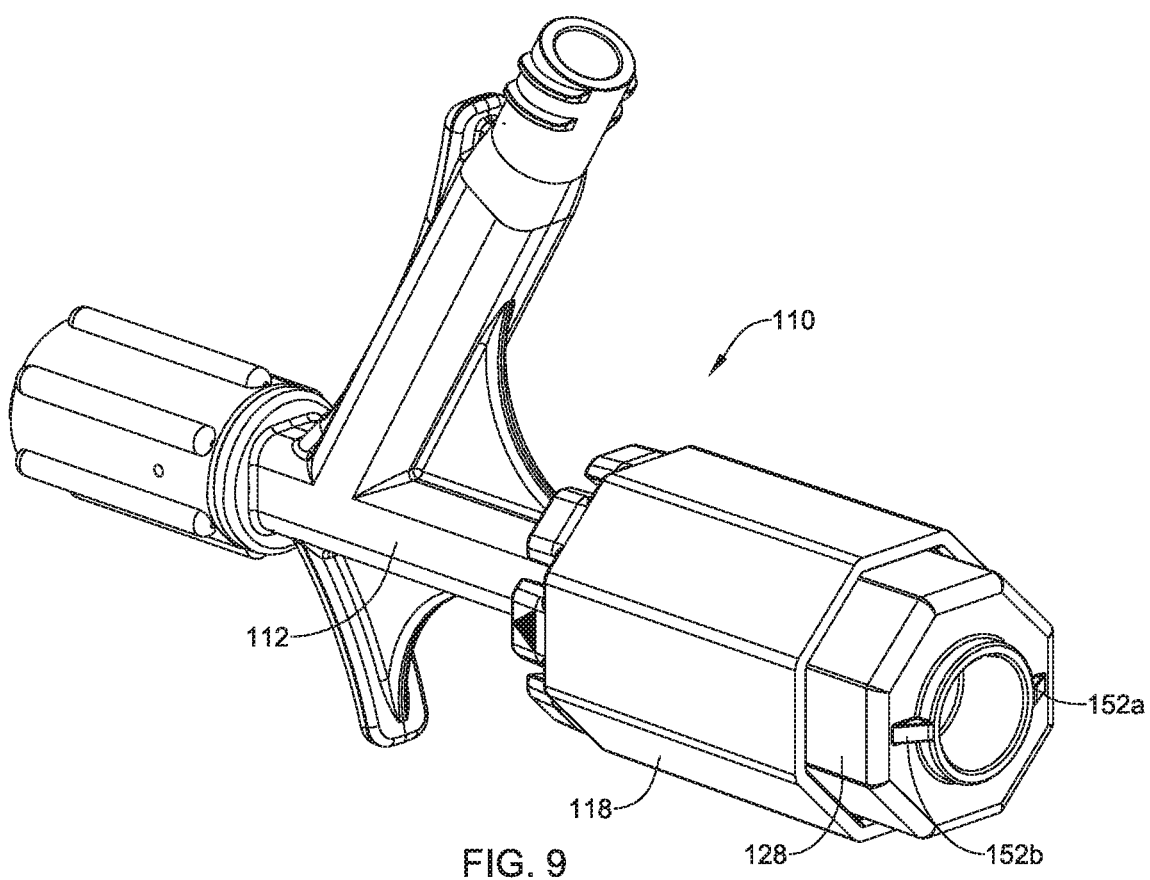

As shown in FIG. 8, the nut 128 may include one or more alignment tabs 152a/152b. In this example, the nut 128 includes two alignment tabs 152a/152b. However, other numbers are contemplated including one, three, four, five, six, or more alignment tabs. The alignment tabs 152a/152b can be aligned with the axial slot(s) 148 formed in the proximal end region 122 of the main body 112. In this example, the proximal end region 122 of the main body 112 includes two opposing axial slots 148 and each of the alignment tabs 152a/152b is aligned with one of the axial slots 148. The nut 128 can then be rotated in a clockwise direction to secure the nut 128 to the proximal end region 122 of the main body 112 as schematically depicted in FIG. 9. In this example, the alignment tab 152a is rotated 180 degrees relative to the proximal end region 122 of the main body 112. This is represented by the alignment tab 152a being aligned with the axial slot 148 along the left side of the proximal end region 122 of the main body 112 in FIG. 8 and then, after rotation, the alignment tab 152a being rotated 180 degrees so as to be aligned with the axial slot 148 (not shown in FIG. 9) along the right side of the proximal end region 122 of the main body 112. This amount of rotation may be suitable to secure the nut 128 to the proximal end region 122 and provide the desired amount of force on the cartridge 120 and/or the second seal member. However, other amounts of rotation are contemplated. For example, the nut 128 may be rotated 45-315 degrees, or about 45-270 degrees, or about 90-180 degrees. In some instances, the nut 128 may be rotated about 45 degrees, about 90 degrees, about 135 degrees, about 180 degrees, about 215 degrees, about 270 degrees, or about 315 degrees.

Figure 10:
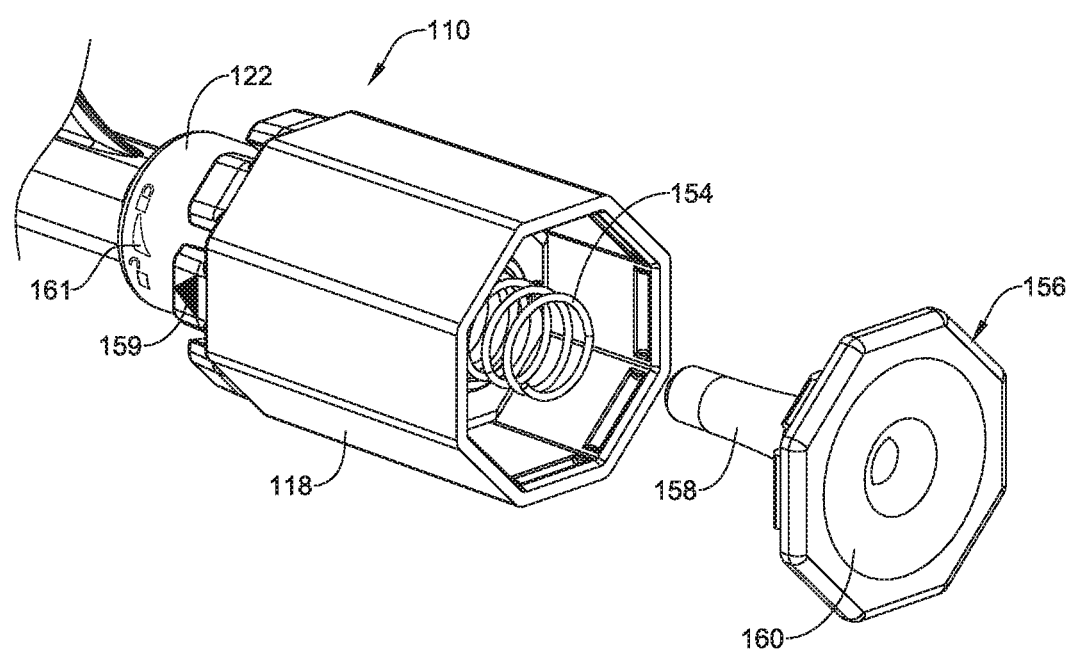

The plunger 118 can be moved proximally as shown in FIGS. 9-10. When the plunger 118 is moved proximally beyond the nut 128 as depicted in FIG. 10, a spring member 154 may be disposed within the nut 128. A plunger cap 156 may be then coupled to the plunger 118. The plunger cap 156 may include an inner tubular region 158 and a proximal end region 160.

As also shown in FIG. 10, the proximal end region 122 of the main body 112 may include a first locking indicator 161. The plunger 118 may include a second locking indicator 159. The locking indicators 161/159 may vary but, in general, may include visual indicators that are designed to communicate to a user which direction (e.g., clockwise) the plunger 118 can be rotated to close the second seal member. The locking indicators 161/159 can vary from what is shown. Proximally retracting the plunger 118 may include aligning the first locking indicator 161 with the second locking indicator 159.

Other manufacturing methods are contemplated. In at least some of these instances, the plunger 118 may be "pre-assembled". For example, the plunger cap 156 may be secured to the plunger 118. The spring member 154 may be loaded into the plunger 118 (e.g., over the inner tubular region 158) and the nut 128 may be loaded into the plunger 118. This subassembly may be brought into engagement with the proximal end region 122 of the main body 112. This may include advancing the locking tab 141 through the opening 137 of the ring member 136 and engaging the nut 128 with the threads 130. The locking tab 141 may be positioned along the distal end of the plunger 118 and project radially inward. The plunger 118 can be rotated to engage the nut 128 with the threads 130. While doing so, the locking indicator 159 may be utilized to track the amount of rotation of the plunger 118 (e.g., and/or the nut 128) so that the nut 128 can be threaded onto the threads 130 the desired amount.

Figure 11:
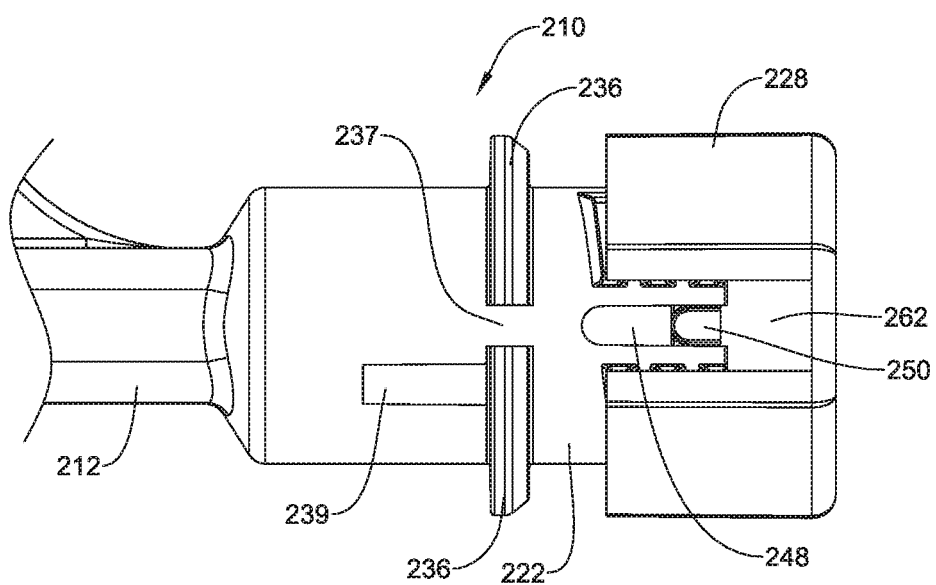
FIG. 11-12 illustrate an example hemostasis valve and an example method for assembling the hemostasis valve.
Figure 12:
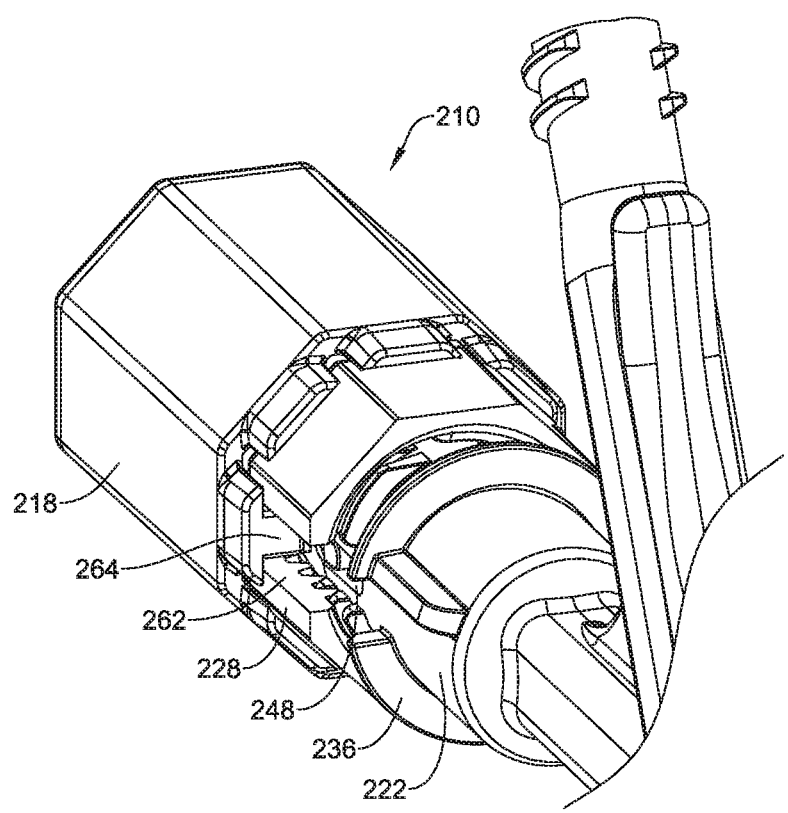

FIGS. 11-12 illustrate a portion of an example hemostasis valve 210 that may be similar to other hemostasis valves disclosed herein and illustrate the process for assembling the hemostasis valve 210. While only a portion of the hemostasis valve 210 is shown, it can be appreciated that the hemostasis valve 210 may include structures similar to or the same as those in the hemostasis valves 10/110 described above. The proximal end region 222 of the main body 212 includes one or more axial slots 248. In this example, the proximal end region 222 includes a pair of opposed axial slots 248. A ring member 236 may also be disposed adjacent to the proximal end region 222. The ring member 236 may have an opening 237 formed therein. A locking rib 239 may be disposed adjacent to the ring member 236.

The method of assembling the hemostasis valve 210 may include disposing a second seal member (not shown, but may be similar to the second seal member 26) and a cartridge at least partially within the proximal end region 222 of the main body 212. While the entire cartridge is not shown a projection 250 of the cartridge, similar to the projection 150, can be seen in FIG. 11. The nut 228 may be disposed adjacent to and/or otherwise engaged with the proximal end region 222. When doing so, a slot 262 formed in the nut 228 may be aligned with the axial slot 248. The nut 228 may be rotated (e.g., in a clockwise direction) a suitable amount to secure the nut 228 to the proximal end region 222. This is represented by the slot 262 in the nut 228 being aligned with the axial slot 248 along the left side of the proximal end region 222 of the main body 212 in FIG. 11 and then, after rotation, the slot 262 in the nut 228 is rotated 180 degrees so as to be aligned with the axial slot 248 on the opposite side of the proximal end region 222 of the main body 212 as shown in FIG. 12. The amount of rotation may vary. For example, the nut 228 may be rotated about 45-315 degrees, or about 45-270 degrees, or about 90-180 degrees, or about 45 degrees, or about 90 degrees, or about 135 degrees, or about 180 degrees, or about 215 degrees, or about 270 degrees, or about 315 degrees.

Once the nut 228 is secured in the desired manner to the proximal end region 222, the plunger 218 may be slid over the nut 228. When doing so, a locking tab 264 may passed through the slot 262 in the nut 228. This may include passing at least a portion of the plunger 218 over or through an opening a ring member 236 disposed along the proximal end region 222 of the main body 212.

It can be appreciated that the assembly process for the hemostasis valve 210, for example because of the slot 262 in the nut 228, allows for a single-piece plunger 218 to be used (as contrasted with the 2-piece plunger 118 shown in FIGS. 6-10).

The materials that can be used for the various components of the hemostasis valve 10 (and/or other hemostasis valves disclosed herein) and the various components thereof disclosed herein may include those commonly associated with medical devices. For simplicity purposes, the following discussion makes reference to the main body 12 and other components of the hemostasis valve 10. However, this is not intended to limit the devices and methods described herein, as the discussion may be applied to other hemostasis valves and/or components thereof disclosed herein.

The main body 12 and/or other components of the hemostasis valve 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for assembling a hemostasis valve, the method comprising:
    positioning a plunger along an outer surface of a threaded proximal end region of a main body;
    wherein the threaded proximal end region of the main body includes one or more threads and an axial slot extending through the one or more threads;
    disposing a cartridge at least partially within the threaded proximal end region of the main body, the cartridge comprising a protrusion, the protrusion is engaged by the axial slot of the threaded proximal end region of the main body;
    advancing the plunger along the outer surface of the threaded proximal end region of the main body to a position where a proximal end of the plunger is disposed distally of at least a portion of the one or more threads;
    disposing a nut adjacent to the threaded proximal end region of the main body, the nut having an alignment tab formed thereon;
    aligning the alignment tab with the axial slot;
    engaging the nut with the one or more threads while the alignment tab is aligned with the axial slot; and
    rotating the nut 45-270° relative to the threaded proximal end region of the main body.

2. The method of claim 1, further comprising disposing a first seal member within the threaded proximal end region of the main body.

3. The method of claim 2, wherein the cartridge comprises a second seal member.

4. The method of claim 3, wherein rotating the nut 45-270° relative to the threaded proximal end region of the main body engages the nut with the cartridge.

5. The method of claim 1, further comprising moving the plunger proximally relative to the threaded proximal end region of the main body.

6. The method of claim 5, further comprising disposing a spring within the plunger.

7. The method of claim 6, further comprising securing a plunger cap to the plunger.

8. The method of claim 1, wherein the threaded proximal end region of the main body has a first locking indicator.

9. The method of claim 8, wherein the plunger includes a second locking indicator and wherein positioning the plunger along a threaded proximal end region of a main body includes aligning the first locking indicator with the second locking indicator.

10. The method of claim 1, wherein rotating the nut 45-270° relative to the threaded proximal end region of the main body includes rotating the nut 90-180° relative to the threaded proximal end region of the main body.

11. The method of claim 1, wherein rotating the nut 45-270° relative to the threaded proximal end region of the main body includes rotating the nut 180° relative to the threaded proximal end region of the main body.

* * * * *